(12) United States Patent
Tachibana

(10) Patent No.: US 10,934,567 B2
(45) Date of Patent: Mar. 2, 2021

(54) METHOD FOR MANUFACTURING BIOFUEL

(71) Applicant: EARTHRECYCLE CO., LTD., Hyogo (JP)

(72) Inventor: Takashi Tachibana, Hyogo (JP)

(73) Assignee: EARTHRECYCLE CO., LTD., Hyogo (JP)

( * ) Notice: Subject to any disclaimer, the term of this patent is extended or adjusted under 35 U.S.C. 154(b) by 121 days.

(21) Appl. No.: 16/225,501

(22) Filed: Dec. 19, 2018

(65) Prior Publication Data

US 2020/0199634 A1 Jun. 25, 2020

(51) Int. Cl.
*C12P 7/64* (2006.01)
*C12N 1/12* (2006.01)
*A01G 33/00* (2006.01)
*C10G 3/00* (2006.01)

(52) U.S. Cl.
CPC .............. *C12P 7/649* (2013.01); *A01G 33/00* (2013.01); *C10G 3/50* (2013.01); *C12N 1/12* (2013.01); *C10G 2400/08* (2013.01)

(58) Field of Classification Search
CPC combination set(s) only.
See application file for complete search history.

(56) References Cited

FOREIGN PATENT DOCUMENTS

| JP | 2012080850 A | * | 4/2012 | ............ C12M 45/04 |
|---|---|---|---|---|
| JP | 2012080850 A | | 4/2012 | |
| JP | 2014161231 A | * | 9/2014 | |
| JP | 2014161231 A | | 9/2014 | |

* cited by examiner

*Primary Examiner* — Ellen M McAvoy
*Assistant Examiner* — Chantel L Graham
(74) *Attorney, Agent, or Firm* — IP Business Solutions, LLC

(57) ABSTRACT

A method for manufacturing a biofuel includes; a step of adding an alkaline agent to a culture fluid in which an algae is cultured and infusing medium quality oil thereto, thereby generating and floating an emulsion; a step of evaporating moisture from the floated emulsion in a vacuum, thereby obtaining a fat and oil component and a solids of the algae and medium quality oil and filtering, thereby separating the fat and oil component of the algae, the medium quality oil and the solids; a step of fractionally distilling the separated fat and oil component of the algae and the separated medium quality oil, thermally decomposing the fractionally-distilled components by adding an alkaline agent thereto, thereby obtaining a pyrolysis oil and a pyrolysis residue, and fractionally distilling the pyrolysis oil into thermally-decomposed gas, light crude oil, medium quality oil and heavy quality oil; and a step of removing an impurity from the fractionally-distilled medium quality oil by means of solvent extraction, thereby obtaining a biodiesel fuel oil.

3 Claims, 1 Drawing Sheet

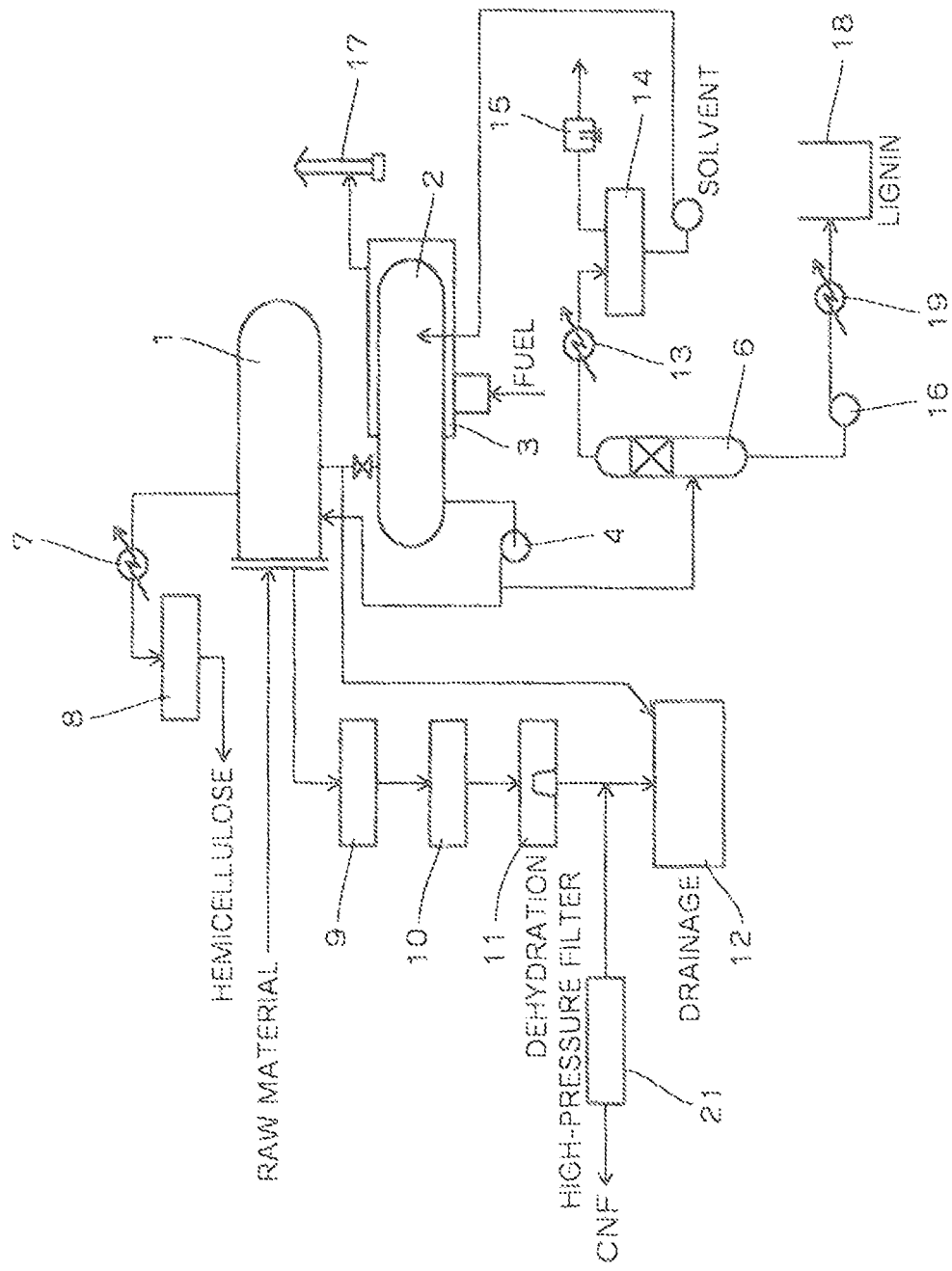

METHOD FOR MANUFACTURING BIOFUEL

CROSS-REFERENCE TO THE RELATED APPLICATION

This application is based on Japanese Patent Application No. 2016-120702 filed on Jul. 17, 2016 and published on Dec. 21, 2017 (JP-A-No. 2017-221162).

BACKGROUND OF THE INVENTION

Field of Invention

The present Invention relates to a method for manufacturing a biofuel and in particularly, to a method for manufacturing a biofuel that can be used in an extensive use due to a fat and oil component produced by algae having a capability of synthesizing a fat and oil component.

Background Art

Recently, there has been a global-scale concern about a problem of resource depletion attributed to the heavy use of fossil fuels or environmental pollution attributed to the combustion of fossil fuels, and the development of alternative energy capable of stably and sustainably supplying energy without relying on fossil fuels has become an urgent task.

As one of such alternative energy, a biofuel that is produced from algae having a capability of synthesizing a fat and oil component is attracting attention.

For example, it is proposed a method in which the algae are cultured, the cultured algae are dried and crushed, a fat and oil component is separated or extracted using a solvent, and the obtained fat and oil component is purified, thereby manufacturing a biofuel (Patent Document 1).

However, for the algae-derived biofuels, complicated processes such as the drying and crushing of cultured algae and the separation or extraction and purification of fat and oil components are required, and the costs are still higher compared with those of fossil fuels, and thus, at the moment, the algae-derived biofuels do not reach a stage of practical use.

In contrast, it was proposed a method in which, for each alga, an emulsion of a fat and oil component produced by the algae are produced and the use of the fat and oil component of the algae as a low-cost biofuel is enabled (Patent Document 2).

RELATED ART DOCUMENT

Patent Document

Patent Document 1: JP-A-2012-080850
Patent Document 2: JP-A-2014-161231

SUMMARY OF THE INVENTION

Technical Problem

However, in the method described in Patent Document 2, a solid component of the algae is included in the biofuel, and thus the use of the biofuel is limited, and there has been a demand for separating or extracting a biofuel that can be used at a low cost and, furthermore, in an extensive uses from the fat and oil component of the cultured algae using a simple process.

An object of the present Invention is to provide a method for manufacturing a biofuel that can be used in an extensive uses due to a fat and oil component produced by the algae at a low cost using a simple process.

Solution Problem

A method for manufacturing a biofuel according to the present Invention includes; a step of adding an alkaline agent to a culture fluid in which the algae having a capability of synthesizing a fat and oil component is cultured and infusing the medium quality oil into the culture tank, thereby generating and floating an emulsion of the medium quality oil and the algae; a step of evaporating moisture from the floated emulsion of the algae by a vacuum evaporation, thereby obtaining a fat and oil component and solids of the algae and medium quality oil and filtering the fat and oil component and the solids of the algae and the medium quality oil, thereby separating the fat and oil component of the algae from the medium quality oil and the solids; a step of fractional-distilling the separated fat and oil component of the algae and the separated medium quality oil, thermal-decomposing the fractionally-distilled components with adding an alkaline agent thereto, thereby obtaining a pyrolysis oil and a pyrolysis residue, and fractional-distilling the pyrolysis oil into pyrolysis gas, light quality oil, medium quality oil and heavy quality oil; and, a step of removing an impurity from the fractional-distilled medium quality oil by means of solvent extraction, thereby obtaining a biodiesel fuel oil.

One of characteristics of the present Invention is to infuse the medium quality oil into a culture tank by adding the alkaline agent thereto, generate and float the emulsion of the algae and the medium quality oil, separate moisture by means of vacuum evaporation, thereby obtaining the fat and oil component and the solids of the algae and the medium quality oil.

Therefore, it is possible to separate the fat and oil component of the algae by using a simpler process than that in a case in which the fat and oil component of the algae is separated by using a method such as centrifugal separation, pressure flotation, agglomeration, or extraction.

A second characteristic of the present Invention is to thermal-decompose the fat and oil component of the algae and the medium quality oil into a pyrolysis oil and a pyrolysis residue.

Therefore, it is possible to manufacture a biodiesel fuel oil by converting the fat and oil component of the algae into a pyrolysis oil of a petroleum composition by using a simple process, the solids of the algae is not included in the biofuel as the manufacturing method described in Patent Document 2, and the biofuel can be used in an extensive uses.

In addition, it is also possible to purify the medium quality by means of hydrogenation and use the medium quality oil as a jet fuel.

Furthermore, in the thermal decomposition of fractional-distilled distillation component, it is also possible to thermally decompose the fractional-distilled distillation components by adding waste food oil, palm nut, palm strained lees, *Jatropha* or the like.

Here, examples of the alga having a capability of synthesizing a fat and oil component can include algae such as *Botryococcus braunii, Chlorella* sp., *Cryptothecodinium cohnii, Cylidrotheca* sp., *Dunaliella primolecta, Isochrysis* sp., *Monallanthus salina, Nannochloris* sp., *Nannochloropsis* sp., *Neochloris oleoabundans.*, *Nitzschia* sp., *Phaeodactylum tricornutum, Schizochytrium* sp., *Tetraselmis suieia*, but it is also possible to use algae other than the above-described algae, that is, the existing algae, algae that will be discovered in the future, and new algae obtained by genetic manipulation as long as the algae produce a fat and oil component.

BRIEF DESCRIPTION OF THE DRAWING

FIG. 1 is a step view schematically illustrating a preferred embodiment of a method for manufacturing a biofuel according to the present Invention.

DETAILED DESCRIPTION OF THE PREFERRED EMBODIMENTS

Hereinafter, the present Invention will be described in detail on the basis of a specific example illustrated in the drawing. FIG. 1 schematically illustrates a preferred embodiment of a method for manufacturing a biofuel according to the present Invention. A system for manufacturing a biofuel includes a culture tank 10, a vacuum evaporation tank 11, a filter 12, a distillation tower 13, a washing tank 14, a fermenting tank 15, a thermal decomposition furnace 16, a fractional distillation tower 17, a solvent extraction tank 18, and a hydrogenation treatment device 19.

In a case manufacturing biofuel, first, a culture fluid and the algae are fed into the culture tank 10, a nitrogen compound is added as a nutrient content for the algae to the culture fluid, and the algae are cultured at room temperature. As the culture fluid, deep ocean water 20 is used, and *Dunaliella* is used as the algae.

The *Dunaliella* includes 15 wt % of triglyceride, 15 wt % of glycerin, 60 wt % of ocean water, and 10 wt % of the solids in a cell membrane of the algae and disperses and floats in the culture fluid.

Next, caustic soda (an alkaline agent) is added to the culture fluid in the culture tank 10, medium quality oil 21 is infused from a tank bottom, an emulsion of the algae and the medium quality oil are generated and floated, the emulsion of the algae is spread in the vacuum evaporation tank 11, and moisture is evaporated in a vacuum. Then, triglyceride which is a fat and oil component of the algae, glycerin, the medium quality oil, and the solids including a chloride derived from a salt content in the ocean water remains on the tank bottom, and thus these components are spread in the filter 12 and separated into the solids including the chloride and triglyceride, glycerin, and the medium quality oil all of which are liquid, the solids are spread in the washing tank 14 and washed, and salt water flowing out due to washing is discharged.

In a case using *Dunaliella* as the algae, the solids include β-carotene, glutathione, and the algae residue, and β-carotene is not soluble in water and has a high pour point of 180° C.

In addition, glutathione is soluble in water, an acid, or an alkali, is decomposed at 62° C., and has a high pour point of 175° C. to 185° C. Therefore, moisture is added to the solids, the salt content and glutathione are dissolved, glutathione is extracted, and then salt water is discharged. β-carotene is extracted from undissolved β-carotene and the algae residue.

Triglyceride, glycerin and the medium quality oil are spread in the distillation tower 13 and fractional-distilled into triglyceride, glycerin and the medium quality oil, and triglyceride and the medium quality oil are sent to the thermal decomposition furnace 16 and thermally decomposed.

Glycerin is sent to the fermenting tank 15 and fermented by adding yeast thereto, whereby a fat and oil is obtained, and the fat and oil is also sent to the thermal decomposition furnace 16 and thermally decomposed.

In addition, triglyceride, glycerin and the medium quality oil are sent to the thermal decomposition furnace 16 and thermally decomposed.

The thermal decomposition is carried out under conditions of normal pressure, a temperature range of 380° C. to 550° C., and three to six hours, and an alkaline agent such as $Ca(OH)_2$ is added thereto. A pyrolysis oil and a pyrolysis residue are obtained due to the thermal decomposition, and the pyrolysis residue can be used as a home fuel.

In addition, in the thermal decomposition, it is also possible to add waste food oil, palm nut, palm strained lees, or *Jatropha* thereto and carry out the thermal decomposition.

The pyrolysis oil is sent to the fractional distillation tower 17 and fractionally distilled into thermally-decomposed gas, light quality oil at thermal of 150° C. or lower, medium quality oil at thermal of 150° C. to 300° C., and heavy quality oil at thermal of 350° C. or higher, pyrolysis residue at thermal of 350° C. or higher, and the medium quality oil is circulated in the culture tank 10 and used to produce an emulsion of the algae In addition, the light quality oil and heavy quality oil can be used as the home fuel.

The yield in the thermal decomposition of triglyceride is set to 80 wt % for the pyrolysis oil, and the yield in the fractional distillation tower 17 is set to 5/5/90 wt % for the decomposed gas/the light quality oil/the medium-heavy quality oil.

The obtained medium quality oil is spread in the solvent extraction tank 18, and impurities (a nitrogen component, a chlorine component and an aroma component) are removed by adding an alcohol-based solvent such as methanol thereto, whereby a high-quality biodiesel fuel oil is obtained.

In addition, the obtained medium quality oil is sent to the hydrogenation treatment device 19, hydrogen is added thereto in an amount at which the aroma component in the fuel oil is saturated, a hydrogenation treatment is carried out, and distillation is carried out, whereby a jet fuel having an improved smoke point is obtained. The hydrogenation is carried out at a reaction temperature of 200° C. to 370° C. and 40 $kg/cm^2$ to 70 $kg/cm^2$ by using a noble metal catalyst.

Meanwhile, a method for manufacturing a biofuel by means of centrifugal separation, pressure flotation, agglomeration or extraction can also be considered, however, in all cases, a great energy is required and the cost also becomes high.

In contrast, the method of the present example is a simpler process than the above-described method, does not require the great energy, and is practically excellent.

In the above description, a case in which *Dunaliella* that lives in deep ocean water is used as the algae has been described, but the method can be applied in the same manner to a case in which, for example, Anistridemus that lives in fresh water, the different algae, or the like is used.

As a result of culturing, dehydrating, thermally decomposing, and fractionally distilling Anistridemus that lives in the fresh water and analyzing individual fractions, the following results were obtained.

| | Thermally-decomposed oil (%) | Light crude oil (%) | Intermediate crude oil (%) | Heavy crude oil (%) |
|---|---|---|---|---|
| C | 78.12 | 80.19 | 80.54 | 82.2 |
| H | 11.05 | 11.46 | 11.70 | 12.1 |
| N | 6.26 | 5.53 | 5.72 | 4.6 |
| O | 3.70 | 1.80 | 1.40 | 0.3 |
| Total sulfur component | 0.35 | 0.19 | 0.10 | 0.0 |
| Chlorine component | Less than 0.01 | 0.02 | Less than 0.01 | 0.0 |
| Total amount of heat generated | 40670 kj/kg | | | |

From the analysis results described above, it was confirmed that the fat and oil component of the algae can be converted to a petroleum composition by adding the alkaline agent to the alga and thermally decomposing the algae.

What is claimed is:

1. A method for manufacturing a biofuel, comprising:
   a step of adding an alkaline agent to a culture fluid in which the algae having a capability of synthesizing a fat and oil component is cultured and infusing medium quality oil thereto, thereby generating and floating an emulsion of the medium quality oil and the algae;
   a step of evaporating moisture from the floated emulsion of the medium quality oil and the algae in a vacuum evaporation tank, thereby obtaining a fat and oil component and a solids of the algae and medium quality oil and filtering the fat and oil component and the solids of the algae and the medium quality oil, thereby separating the fat and oil component, the medium quality oil, and the solid matter;
   a step of fractionally distilling the separated fat and oil component of the algae and the separated medium quality oil, thermally decomposing the fractionally-distilled components by adding an alkaline agent thereto, thereby obtaining a pyrolysis oil and a pyrolysis residue, and fractionally distilling the pyrolysis oil into thermally-decomposed gas, light quality oil, medium quality oil and heavy quality oil; and
   a step of removing an impurity from the fractionally-distilled medium quality oil by means of solvent extraction, thereby obtaining a biodiesel fuel oil.

2. The method for manufacturing a biofuel according to claim 1, wherein a hydrogenation treatment is carried out on the medium quality oil obtained by the fractional distillation by adding hydrogen thereto, thereby obtaining a jet fuel.

3. The method for manufacturing a biofuel according to claim 1, wherein in the thermal decomposition of the fractionally-distilled components into the pyrolysis oil and the pyrolysis residue, the fractionally-distilled components are thermally decomposed by adding waste food oil, palm nut, palm strained lees, or Jatropha thereto.

* * * * *